US011730610B2

(12) United States Patent
Breuninger et al.

(10) Patent No.: US 11,730,610 B2
(45) Date of Patent: Aug. 22, 2023

(54) ARTIFICIAL FOOT

(71) Applicant: MECURIS GMBH, Munich (DE)

(72) Inventors: Jannis Breuninger, Grossbettlingen (DE); Franziska Glas, Munich (DE); Bence Rochlitz, Munich (DE); Carolin Taubmann, Neuhaus (DE); Clemens Rieth, Boeblingen (DE)

(73) Assignee: MECURIS GMBH, Munich (DE)

( * ) Notice: Subject to any disclaimer, the term of this patent is extended or adjusted under 35 U.S.C. 154(b) by 187 days.

(21) Appl. No.: 17/054,374

(22) PCT Filed: May 8, 2019

(86) PCT No.: PCT/EP2019/061838
§ 371 (c)(1),
(2) Date: Nov. 10, 2020

(87) PCT Pub. No.: WO2019/219482
PCT Pub. Date: Nov. 21, 2019

(65) Prior Publication Data
US 2021/0369473 A1   Dec. 2, 2021

(30) Foreign Application Priority Data
May 14, 2018 (DE) ................. 20 2018 102 687.9

(51) Int. Cl.
*A61F 2/66* (2006.01)
(52) U.S. Cl.
CPC ........ *A61F 2/66* (2013.01); *A61F 2002/6664* (2013.01); *A61F 2002/6685* (2013.01)

(58) Field of Classification Search
CPC ...... A61F 2/66; A61F 2/76; A61F 2002/5072; A61F 2002/6614; A61F 2002/6664; A61F 2002/6685; A61F 2/6671; A61F 2/6642; A61F 2/5009
See application file for complete search history.

(56) References Cited

U.S. PATENT DOCUMENTS

| 3,766,569 A | 10/1973 | Orange |
| 5,766,264 A * | 6/1998 | Lundt .................. A61F 2/6607 623/47 |
| 5,769,896 A * | 6/1998 | Rosendahl ............... A61F 2/66 623/49 |
| 6,197,066 B1 | 3/2001 | Gabourie |
| 10,299,942 B2 | 5/2019 | Mosler et al. |
| 10,299,943 B2 | 5/2019 | Clausen et al. |

(Continued)

FOREIGN PATENT DOCUMENTS

| DE | 10053259 A1 * | 10/2001 | .............. A61F 2/66 |
| DE | 102014006727 | 10/2015 | |

(Continued)

OTHER PUBLICATIONS

Patent Cooperation Treaty: International Search Report and Written Opinion for PCT/EP2019/061838; Nils Kickler; dated Jul. 15, 2019; 18 pages.

*Primary Examiner* — Christie Bahena
(74) *Attorney, Agent, or Firm* — Gregory M. Howison (57) ABSTRACT

The invention relates to a prosthetic foot comprising a base body having a main spring element, an upper spring element, a heel spring element, and a front spring element. The base body is formed in one piece.

18 Claims, 4 Drawing Sheets

(56) References Cited

U.S. PATENT DOCUMENTS

| | | | |
|---|---|---|---|
| 2005/0060045 A1* | 3/2005 | Smith | A61F 2/66 623/49 |
| 2005/0203640 A1* | 9/2005 | Christensen | A61F 2/66 623/55 |
| 2005/0267603 A1* | 12/2005 | Lecomte | A61F 2/66 623/50 |
| 2010/0042228 A1* | 2/2010 | Doddroe | A61F 2/76 623/53 |
| 2014/0277587 A1* | 9/2014 | Colvin | A61F 2/66 623/54 |
| 2015/0374514 A1 | 12/2015 | Clausen et al. | |
| 2016/0008147 A1* | 1/2016 | Marlin | A61F 2/66 623/55 |

FOREIGN PATENT DOCUMENTS

| | | | | |
|---|---|---|---|---|
| DE | 202015007994 U1 | 11/2016 | | |
| EP | 2644167 A1 * | 10/2013 | | A61F 2/66 |
| WO | 0027317 A1 | 5/2000 | | |
| WO | WO-2011066354 A2 * | 6/2011 | | A61F 2/66 |

* cited by examiner

ARTIFICIAL FOOT

CROSS-REFERENCE TO RELATED APPLICATIONS

This application is a U.S. National Phase application submitted under 35 U.S.C. § 371 of Patent Cooperation Treaty application serial no. PCT/EP2019/061838, filed May 8, 2019, and entitled ARTIFICIAL FOOT, which application claims priority to German Utility Model Application serial no. 20 2018 102 687.9, filed May 14, 2018, and entitled ARTIFICIAL FOOT.

Patent Cooperation Treaty application serial no. PCT/EP2019/061838, published as WO 2019/219482 A1, and German Utility Model Application serial no. 20 2018 102 687.9, are incorporated herein by reference.

TECHNICAL FIELD

The invention relates to a prosthetic foot for use in a leg or a foot prosthesis.

BACKGROUND

A prosthetic foot is known from DE 20 2015 007 994. Prosthetic feet are exposed to extremely high loads. For this reason, existing prosthetic feet are manufactured from plastics, fiber-reinforced materials and/or metal alloys using injection molding or lamination processes. Prosthetic feet, which are produced using additive manufacturing processes, also known as 3D printing, are known from DE 10 2014 006 727 B3.

There are a number of aspects that are important for fulfilling the functional requirements of a prosthetic foot. The damping properties, which are most evident upon heel impact, are essential to comfort when walking. The geometry of the sole is important for a harmonious rolling behavior during walking. Also desirable, and usually achieved by means of passive spring elements, is an energy return when the forefoot is lifted off the ground. This ensures energy-efficient walking for the prosthesis wearer.

An individual, patient-specific design of the overall prosthesis is generally important in order to adapt the functional elements to the needs of the patient. Conventional prosthetic feet, however, allow only limited individual modifications. For the most part, it is not the prosthetic foot itself that is modified. Rather the certified prosthetist/orthotist selects a foot that best matches the desired properties from the many different prosthetic feet. Prosthetic feet are usually also available in different sizes. Some can still be adapted, for example, by exchanging or adjusting the damping elements.

The additively manufactured prosthetic feet currently still in development offer the possibility of individually adapting each individual prosthetic foot using tool-free production. Thus, not only the foot size can be adjusted, but also, to a particularly high degree, the damping properties and the rollover behavior.

However, the materials available for these processes do not currently provide the spring properties and thus the energy return that can be achieved, for example, with conventionally manufactured, fiber-reinforced plastics.

Prosthetic feet furthermore also have to meet target group-specific requirements. Consequently, there are prosthetic feet have been developed specifically for sports. Another example is older people, who are in a standing phase more often than young people.

SUMMARY

Based on this state of the art, it is the object of the present invention to provide an improved prosthetic foot, in particular an improved foot prosthesis. A further object is to design the prosthetic foot in such a way that a higher degree of individualization is made possible in a simple and cost-effective manner. The production costs should be as low as possible and the comfort of the user should be as high as possible. It should furthermore be possible to wear the prosthetic foot comfortably, especially during a standing phase.

This object is achieved by a prosthetic foot according to claim 1.

The object is in particular achieved by a prosthetic foot, in particular a foot prosthesis, comprising a base body having a main spring element, an upper spring element, a heel spring element, and a front spring element, wherein the base body is formed in one piece.

A core aspect of the invention is therefore to create a prosthetic foot in which the essential elements are formed in one piece. The one-piece design permits particularly efficient production, for example using additive manufacturing processes. This saves costs and production time. By using a total of four spring elements, it is also possible to create a particularly good adjustment of the spring properties to the user. It is also advantageous that the base body comprises a heel spring element and a front spring element. The heel spring element can serve to cushion the heel when the user puts his foot down. The front spring element, on the other hand, can serve to provide a flexible structure when the foot is lifted off the ground. The prosthetic foot can thus be optimally designed for every phase of walking.

In one embodiment, the prosthetic foot can be made of a thermoplastic material. The prosthetic foot can in particular be produced in an additive manufacturing process, for example a 3D printing process.

The advantage of the described embodiment is that the prosthetic foot can be produced individually for each patient. It is also possible to adapt different parameters of the prosthetic foot to the user. For example, the thickness of individual regions of the prosthetic foot can be adjusted to the weight and/or size of the user.

In one embodiment, the upper spring element and the heel spring element can be connected to one another via the main spring element, wherein the heel spring element can be configured to be brought at least partially into contact with the main spring element under load.

The main spring element can be disposed above the heel spring element. Thus, when a user steps on the prosthetic foot, the heel spring element can deform in such a way that the heel spring element is pressed against the main spring element. This results in two different spring effects. On the one hand, the main spring element is pressed downward and, on the other hand, the heel spring element is pushed upward. This makes placing the foot on the ground particularly soft and comfortable. The main spring element furthermore serves as a stop element, so that the movement of the spring elements is limited. If there is contact between the main spring element and the heel spring element, the force when placing the foot on the ground is optimally transmitted to the leg of the user. This reduces the force that is absorbed by the material.

In one embodiment, the heel spring element can comprise a stop surface on its upper side, which is configured to be brought at least substantially into contact with a correspondingly shaped stop surface disposed on the main spring element.

In order to reduce material wear, the stop surface of the main spring element and the heel spring element can be configured adapted to one another. An optimal result is achieved when the stop surface of the heel spring element rests flat on the stop surface of the main spring element. In this case, the force that is introduced into the prosthetic foot when the foot is placed on the ground is transported over a large area in the direction of the leg of the user.

In one embodiment, the stop surfaces can be at least substantially straight. In a further embodiment, the stop surfaces can be curved. The stop surface of the heel spring element can be convex, for example, and the stop surface of the main spring element can be concave. This embodiment has the additional advantage that the surfaces do not move relative to one another, i.e. rub against one another, as a result of the deformation of the material in contact. This further reduces material wear. The stop surface of the main spring element can, of course, also be convex and the stop surface of the heel spring element can be concave.

In one embodiment, the main spring element can comprise a stop, which can be disposed and configured to project from the main spring element to the rear, wherein the stop can comprise a passage from the left to the right side of the prosthetic foot.

The main spring element can be extended to the rear through the stop, so that the stop has substantially no effect on the spring properties of the main spring element. It is also possible for the stop to comprise a passage, which can save material and makes the prosthetic foot lighter.

In one embodiment, the heel spring element can comprise a front and a rear end, wherein a rolling element which extends rearward from a ground plane can be disposed at the rear end of the heel spring element.

A rolling element facilitates rolling when the prosthetic foot is placed on the ground. This results in improved wearing comfort. It also prevents edges of the prosthetic foot from breaking off. Lastly, a further spring component is provided as well, which absorbs forces in a different direction than the rest of the heel spring element.

In one embodiment, the heel spring element can comprise an at least substantially straight underside.

A particularly easy to manufacture embodiment is obtained when the underside of the heel spring element is substantially straight, i.e. substantially parallel to a ground plane. This also has the advantage that the prosthetic foot can be worn in any shoe that has a straight bottom surface, for example certain athletic shoes.

In one embodiment, the heel spring element can have a shape that is at least partially concave when viewed from the side.

A shape that is concave when viewed from the side extends the possible spring deflection of the heel spring element, which leads to a further improved wearing comfort of the prosthetic foot.

In one embodiment, the prosthetic foot can comprise an adapter which can be connected to the base body and can be configured such that it can be disposed in an adapter receptacle in the base body.

An adapter can be used to connect the prosthetic foot to the rest of the structure of a prosthesis. This adapter can be configured as a pyramid adapter, for example. This results in a particularly secure connection between the prosthetic foot and the rest of the prosthesis.

In one embodiment, the adapter can be configured to be connected to the base body by means of an adapter screw.

A particularly secure connection is achieved when an adapter screw is used. The adapter screw can be inserted from below through the prosthetic foot, for example, wherein a stop can be provided to which the adapter screw can be fixed with the aid of a washer. This provides a particularly easy to assemble arrangement.

In one embodiment, the upper spring element can form a spring gap with the main spring element.

The upper spring element and the main spring element can be arranged such that they are opposite to one another. When the foot is lifted off the ground, due to the introduced force, the main spring element moves toward the upper spring element in such a way that the spring elements come into contact. The force is thus optimally transmitted. In one embodiment, the spring elements are configured such that the stop surfaces of the main spring element and the upper spring element come into contact. The area of the force transmission is thus increased.

In one embodiment, the main spring element and the heel spring element can be connected to one another via a connecting element, wherein the connecting element and the main spring element can be disposed on one side of the spring gap and the upper spring element can be disposed on the opposite side of the spring gap.

In one embodiment, the main spring element and the heel spring element are connected to one another in the range from 40% to 60%, in particular 50%, by means of the connecting element.

It is therefore also possible for a connecting element to be provided, which connects the individual spring elements to one another. This connecting element can be configured such that there is an open connection from the left side of the prosthetic foot to the right side of the prosthetic foot. Additional material can thus be saved. The connecting element can furthermore be configured such that it can come into contact with the upper spring element in a form-locking manner when the prosthetic foot is loaded by being placed on the ground. This prevents further material wear.

In one embodiment, the front spring element can have an at least substantially convex shape when viewed from the side.

The convex shape of the front spring element when viewed from the side provides a pleasant feeling when the foot is lifted off the ground. The aforementioned shape further provides that the foot position when the foot is lifted off the ground can be determined in such a way that an optimal introduction of force from the adapter via the upper spring element and the connecting element to the front spring element is made possible.

In one embodiment, the front spring element can comprise a left spring leaf and a right spring leaf, which are disposed at least substantially parallel to one another in the longitudinal direction of the prosthetic foot and are configured spaced apart from one another by a separating gap.

Dividing the front spring element into two separate spring leaves ensures better lateral support. In particular if there is an unevenness in the ground, twisting or the presence of strong lateral forces can be prevented.

In one embodiment, the heel spring element can comprise a tool opening, in particular on its underside.

To mount the adapter, the heel spring element can comprise a tool opening, so that a tool can be guided from below through the prosthetic foot to the adapter mount. For example, a hexagonal wrench, a spider wrench or a slot wrench can be guided by the tool opening. The maintenance or assembly of the prosthetic foot is thus greatly simplified.

In one embodiment, the tool opening and the separating gap can be configured connected to one another via the connecting element.

It is therefore possible for the separating gap to extend from the front end of the prosthetic foot to the tool opening. The advantages achieved by the separating gap are thus available over almost the entire length of the prosthetic foot.

In one embodiment, the base body can comprise a stop which can be disposed above the upper spring element. In one embodiment, the stop is configured such that the stop and the upper spring element can be brought into contact when the foot is pushed off the ground. This ensures greater flexibility of the base body during a resting phase and at the same time good force transmission when pushing off the ground.

A secondary aspect of the invention relates to a set consisting of a prosthetic foot and a cosmetic, comprising:
 a prosthetic foot as described above, and a cosmetic
 wherein the prosthetic foot is configured to be disposed at least partially within the cosmetic.

Embedding the prosthetic foot in a cosmetic results in a pleasant outward appearance and serves as protection against damage to the prosthetic foot.

The invention is explained in more detail below with reference to the two figures.

DETAILED DESCRIPTION

In the following, the same reference numbers are used for parts that are the same or have the same effect.

Figure 1:
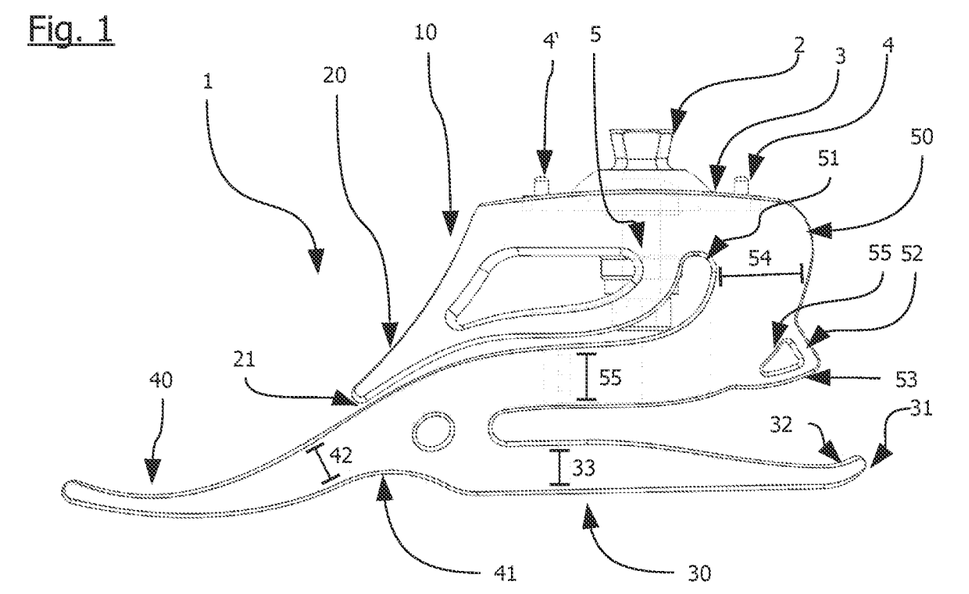
FIG. 1: a prosthetic foot in a first embodiment in a lateral view.

In the following, the region corresponding to the front region of the foot is referred to as the front region, i.e. the left region of FIG. 1, and the region corresponding to a rear region of the foot, i.e. the right region of FIG. 1, is referred to as the rear region of the prosthetic foot 1.

FIG. 1 shows a prosthetic foot 1 in lateral view. The prosthetic foot 1 comprises a base body 10, which has an upper spring element 20, a front spring element 40, a main spring element 50 and a heel spring element 30. The prosthetic foot 1 is made in one piece of a thermoplastic material. The shown design example is the result of an additive manufacturing process.

The heel spring element 30 comprises an underside, which extends substantially parallel to a ground plane and is closed at the rear end by a rolling element 31. The rolling element 31 has a stop surface 32 on its upper side. The main spring element 50 comprises a stop 52, which is configured to correspond to the stop surface 32 and comprises a correspondingly configured stop surface 53.

When walking, in particular when placing the prosthetic foot 1 on the ground, the rolling element 31 comes into contact with the ground first. The occurring force deforms the heel spring element 30 such that it moves in the direction of the main spring element 50. The main spring element 50 is correspondingly deformed as well. The stop surfaces 32, 53 thus move toward one another until they come into contact. The distance between the stop surfaces 32, 53 therefore determines the spring deflection and essentially the wearing comfort of the prosthetic foot 1. To adapt the prosthetic foot 1 to the weight of the user, the thickness 33 of the heel spring element 30 and the thickness 55 of the main spring element 50 can be adapted to the weight of the user. In particular the maximum thickness can be adjusted in each case.

The length of the heel spring element 30 can moreover be adjusted to change the spring properties of the prosthetic foot 1. It is also possible to modify the shape of the heel spring element 30. In the shown design example, the heel spring element 30 is configured in a front region having the same thickness 33. However, the thickness decreases from the center of the heel spring element 30 to the rolling element 31. The behavior of the heel spring element 30 is thus customizable.

Figure 3:
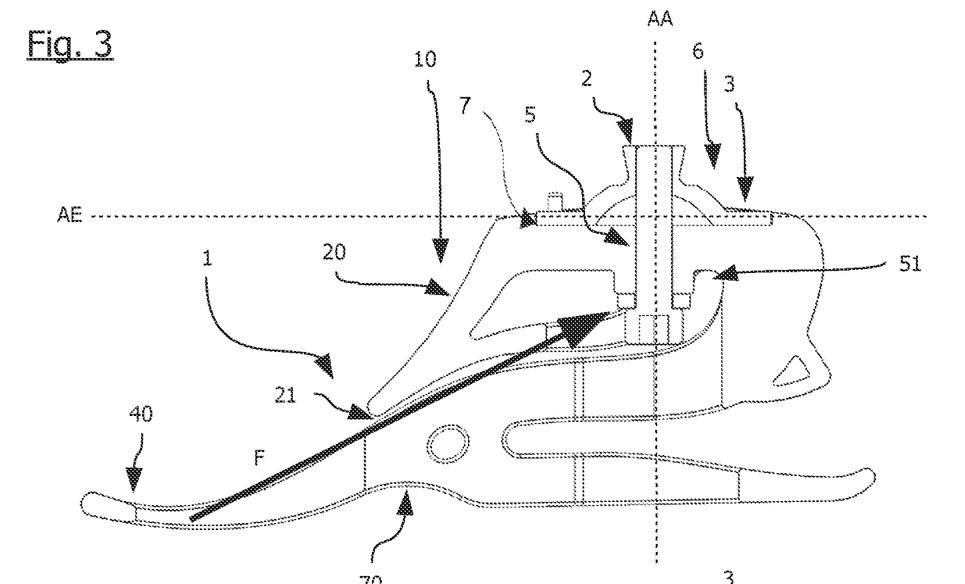
FIG. 3: a lateral sectional view of the prosthetic foot of the first embodiment.

The heel spring element 30 is connected to the front spring element 40 and the main spring element 50 via a connecting element 70 (see FIG. 3). The spring properties of the main spring element 50 can be modified by changing the thickness 55 and the thickness 54. As shown in FIG. 1, the main spring element 50 extends from the connecting element 70 to the rear part of the prosthetic foot 1 substantially parallel to the heel spring element 30, i.e. horizontal to a ground plane. In approximately the rear third of the prosthetic foot 1, the main spring element 50 extends substantially vertically to the ground plane. In the rear and upper region, the main spring element 50 is delimited by an adapter receptacle 7. In the front and central region, the main spring element 50 is delimited by a spring gap 21. The spring gap 21 separates the main spring element 50 from the upper spring element 20.

The upper spring element 20 extends in a lower region above the connecting element 70 and above the main spring element 50. In the shown design example, the upper spring element 20 comprises a passage which extends from the left side of the prosthetic foot 1 to the right side of the prosthetic foot 1. In its upper region, the upper spring element 20 is delimited by an adapter receptacle 7.

In the shown design example, an adapter plate 3 is disposed in the adapter receptacle 7, which is screwed into the base body 10 via adapter screws 4, 4'. A pyramid adapter 2, which is held from below by an adapter screw 5, can be inserted into the adapter plate. The adapter screw 5 can be guided through the prosthetic foot 1 from below, whereby the adapter screw 5 is screwed to the pyramid adapter 2. For this purpose, a stop is provided in the upper spring element 20, against which the screw 5 is held.

The spring gap 21 extends between the upper spring element 20 and the main spring element 50. In the side view shown in FIG. 1, the spring gap 21 ends behind the adapter screw 5 or the pyramid adapter 2. Consequently, when a lateral force acts on the pyramid adapter 2, the upper spring element 20 is pressed onto the main spring element 50 or onto the connecting element 70. This is essential, in particular, when a user wants to push himself off the ground while walking. To do this, it is necessary for the force introduced by the pyramid adapter 2 to be transmitted to the front spring element 40.

The front spring element 40 tapers from the connecting element 70 toward the front. The tapered shape in particular increases the flexibility in the front part. The front spring element 40 further comprises a spring element width 42, which contributes to determining the spring properties of the front spring element 40. By adjusting the spring element width 42, the front spring element 40 can be adapted to the weight of the user. The front spring element 40 has a curved shape which extends upward in the front region, i.e. away from the ground plane.

Figure 2:
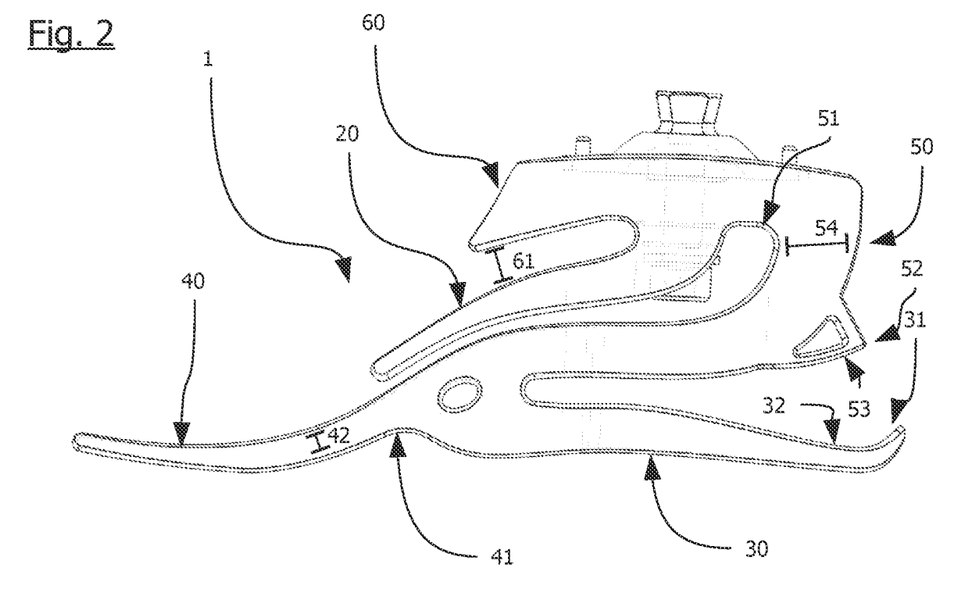
FIG. 2: a prosthetic foot in a second embodiment in a lateral view.

FIG. 2 shows a second embodiment of the invention. In the embodiment of FIG. 2, the base body 10 additionally comprises a stop 60. In the front region, the stop 60 is disposed spaced apart from the upper spring element 20 by a spring width 61. The spring width 61 is wider than the spring gap 21. The prosthetic foot 1 consequently has greater freedom of movement during a standing phase. The spring width 61 can in particular be twice as wide as the spring gap 21.

In contrast to FIG. 1, the heel spring element 30 of the embodiment of FIG. 2 has a curved underside. The shape of the underside of the heel spring element 30 results in extended spring deflection. The spring deflection can thus be extended in a simple manner without negatively affecting the stability of the main spring element 50.

The second embodiment also comprises a further configuration of the rolling element 31. The rolling element 31 of FIG. 2 extends almost vertically to a ground plane. When the rolling element 31 comes into contact with the stop element 52, it engages behind the stop element 52. The stop element 52 is thus protected from environmental influences at the moment when the greatest force acts on the heel spring element 30.

FIG. 3 shows a lateral sectional view of the first embodiment. A force vector F showing the force transmission from the ground into the adapter 2 is drawn in FIG. 3. Typically, only the front end of the front spring element 40 will be in contact with the ground when pushing off the ground. The shown embodiment ensures that the occurring force F is transmitted as directly as possible into the adapter 2, and thus into the rest of the prosthesis. When the foot is lifted off the ground, a lateral force is exerted on the upper spring element 20 and the main spring element 50 via the adapter 2, which causes the spring gap 21 to close. The force is consequently transmitted to the front spring element 40. This results in a deformation of the front spring element 40.

In the shown embodiment, the adapter plate 3, which defines an adapter plane AE, is disposed substantially parallel to a ground plane. A load plane AA extends vertically to the adapter plane AE. During a standing phase, i.e. when the user is standing up straight, a load acts substantially vertically to the ground plane and to the adapter plane AE. A force is thus in particular exerted on the front spring element 20 and the main spring element 50, and a corresponding deformation of the prosthetic foot 1 occurs.

FIG. 3 shows the prosthetic foot 1 of the first embodiment in a lateral perspective view from above. As can be seen in the figure, the adapter screws 4, 4' are disposed on opposite sides of a separating plane that divides the prosthetic foot longitudinally. This ensures that lateral forces acting on the adapter 2 do not cause the adapter plate to tear out of the prosthetic foot 1.

In addition, in the shown embodiment, the front spring element 40 is divided in two. The front spring element 40 comprises right and left spring elements 43, 43', which are disposed spaced apart from one another by a separating gap 44. It is possible for the spring elements 43, 43' to have different spring properties. For example, the elements 43, 43' can have different thicknesses. The thickness of the spring elements 43, 43' can in particular be adapted to the weight of the user of the prosthetic foot 1.

Figure 4:
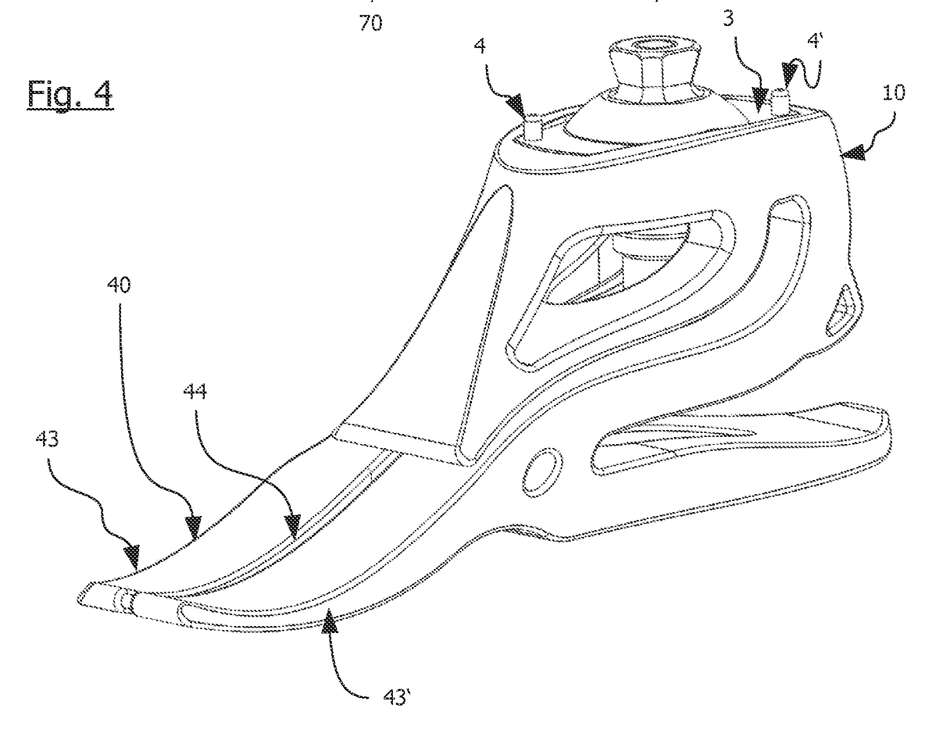
FIG. 4: a perspective view from above onto the prosthetic foot of the first embodiment.
Figure 5:
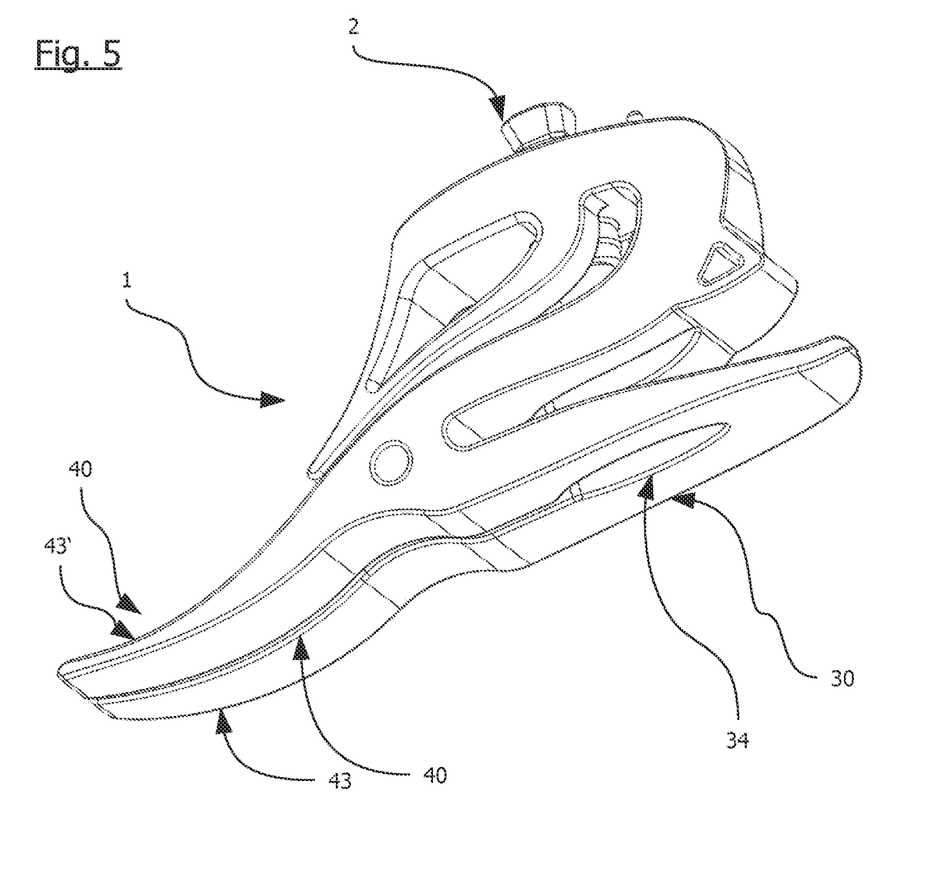
FIG. 5: a perspective view from below of the prosthetic foot of the first embodiment.

FIG. 4 shows embodiment 1 in a lower lateral view. As can be seen in FIG. 4, the separating gap 44 extends from the front spring element 40 to the heel spring element 30. The separating gap 44 is configured such that it opens into a tool opening 34 in the heel spring element 30. The tool opening 34 is designed such that a screwing tool and an adapter screw 5 can be guided through the prosthetic foot 1 from below to screw on the adapter 2.

The entire prosthetic foot 1 can be embedded in a cosmetic. This makes it possible for the prosthetic foot 1 to have an attractive appearance. The cosmetic furthermore protects the prosthetic foot 1 from damage. However, it is also conceivable for the prosthetic foot 1 or a cosmetic to be worn.

Figure 6:
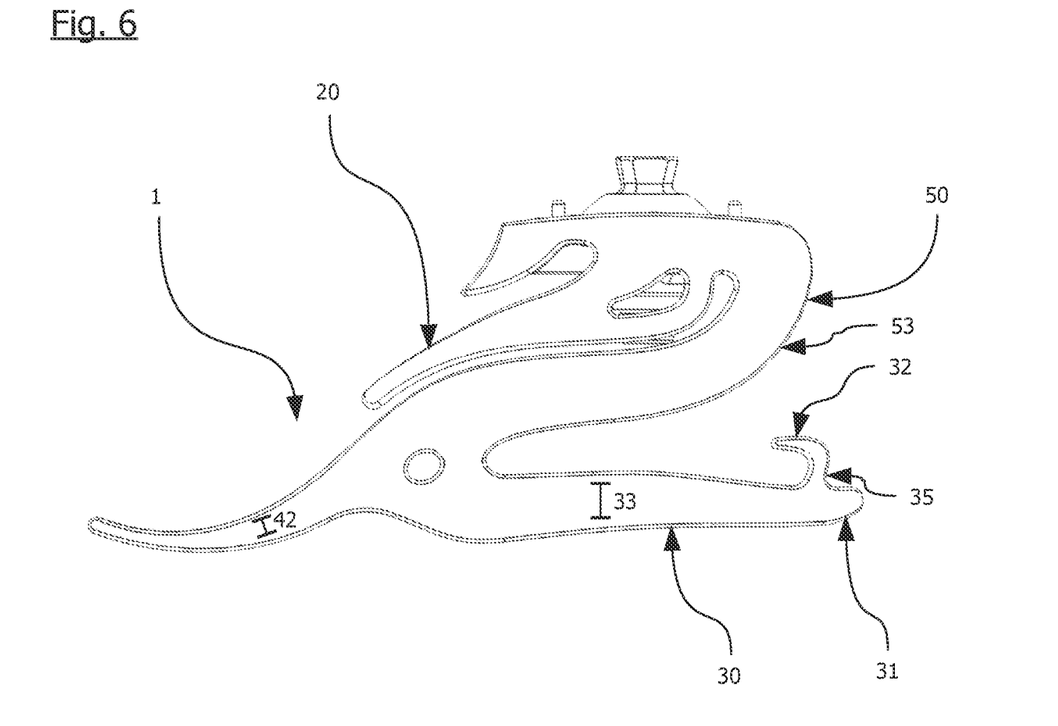
FIG. 6: a prosthetic foot in a third embodiment.

FIG. 6 shows a prosthetic foot 1 in a third embodiment. The prosthetic foot 1 of the third embodiment is substantially similar to the prosthetic foot 1 of FIG. 2, so that the features described with respect to FIG. 2 can also be applied to the embodiment of FIG. 6. Similar to the prosthetic foot 1 of FIG. 2, the prosthetic foot of FIG. 6 comprises a stop 60. A stop surface 32, which is pressed against a stop surface 53 of the main spring element 50 when the user jumps, is additionally provided in the heel region of the prosthetic foot 1.

In the rear region in front of a rolling element 31, the heel spring element 30 comprises a stop element 35 which is configured to project upward from the heel spring element 30. The stop element 35 is hook-shaped, whereby the stop element 35 is bent inward in its upper region, i.e. toward the center of the prosthetic foot. The stop element 35 comprises the stop surface 32 and can be dimensioned such that a secure stop is ensured when the user jumps. The dimensioning of the stop element 35 can in particular be selected taking into account the weight of the user.

REFERENCE SIGNS

1 Prosthetic foot
2 Adapter
3 Adapter plate
4, 4' Adapter plate screw
5 Adapter screw
10 Base body
20 Upper spring element
21 Spring gap
30 Heel spring element/heel body
31 Rolling element
32 Stop surface
33 Spring element width
34 Tool opening
35 Stop element
40 Front spring element
41 Arch
42 Spring element width
43 Right spring element
43' Left spring element
44 Separating gap
50 Main spring element
51 Spring cavity
52 Stop
53 Stop surface
54 Spring element width
55 Passage
60 Stop
61 Spring width 70 Connecting element
F Force
AA Load plane
AE Adapter plane

The invention claimed is:

1. A prosthetic foot, comprising:
a base body having a main spring element, an upper spring element, a heel spring element, and a front spring element,
wherein the base body is formed in one piece,
the main spring element having a lower surface, the heel spring element having an upper surface and a lower surface, the lower surface of the heel spring element for contacting an external ground surface,
a stop disposed on a distal end of the main spring element proximate the lower surface thereof, the stop having a lower surface proximate the lower surface of the main spring element, and
the upper surface of the heel spring element including a heel stop surface on a posterior end thereof and the lower surface of the stop comprising a main stop surface, the main and heel stop surfaces having conforming surfaces when brought into contact with each other,
wherein the main and heel stop surfaces are operable to move towards each other until they come into contact when walking, the distal end of the heel spring element flexing more than an end proximate a mid-portion of the base body.

2. The prosthetic foot according to claim 1, wherein:
the stop comprising a passage from a left side of the prosthetic foot to a right side of the prosthetic foot.

3. The prosthetic foot according to claim 1, wherein:
the distal end of the heel spring element comprises a rolling element which extends rearward from a ground plane.

4. The prosthetic foot according to claim 1, wherein:
the heel spring element comprises a substantially straight underside extending from at least a midportion to a point proximate a distal end of the heel spring element.

5. The prosthetic foot according to claim 1, wherein:
the heel spring element has a shape that is at least partially concave on a portion thereof when viewed from a side of the prosthetic foot.

6. The prosthetic foot according to claim 1, further comprising:
an adapter that is configured to be connected to the base body and that is configured to be disposed in an adapter receptacle in the base body.

7. The prosthetic foot according to claim 6, wherein:
the adapter is configured to be connected to the base body by means of an adapter screw.

8. The prosthetic foot according to claim 1, wherein:
the upper spring element forms a spring gap with the main spring element.

9. The prosthetic foot according to claim 8, wherein:
the main spring element and the heel spring element are connected to one another via a connecting element,
the connecting element and the main spring element are disposed on one side of the spring gap, and
the upper spring element is disposed on an opposite side of the spring gap.

10. The prosthetic foot according to claim 1, wherein:
the front spring element has a substantially convex shape when viewed from a side of the prosthetic foot.

11. The prosthetic foot according to claim 1, wherein:
the front spring element comprises a left spring leaf and a right spring leaf, which are disposed substantially parallel to one another in a longitudinal direction of the prosthetic foot and are spaced apart from one another by a separating gap.

12. The prosthetic foot according to claim 1, wherein:
the heel spring element comprises a tool opening.

13. The prosthetic foot according to claim 12, wherein:
the front spring element comprises a left spring leaf and a right spring leaf, which are disposed substantially parallel to one another in a longitudinal direction of the prosthetic foot and are spaced apart from one another by a separating gap, and
the tool opening and the separating gap are connected to one another via a connecting element.

14. The prosthetic foot of claim 13, wherein:
the main spring element and the heel spring element are connected to one another via the connecting element.

15. The prosthetic foot according to claim 1, wherein:
the base body comprises a stop which is disposed above the upper spring element.

16. The prosthetic foot according to claim 1, wherein:
the prosthetic foot is configured to be disposed at least partially within a cosmetic.

17. A prosthetic foot assembly, comprising:
a prosthetic foot comprising a base body having a main spring element, an upper spring element, a heel spring element, and a front spring element, wherein the base body is formed in one piece;
the main spring element having a lower surface, the heel spring element having an upper surface and a lower surface, the lower surface of the heel spring element for contacting an external ground surface;
a stop disposed on a distal end of the main spring element proximate the lower surface thereof, the stop having a lower surface proximate the lower surface of the main spring element;
the upper surface of the heel spring element including a heel stop surface on a posterior end thereof and the lower surface of the stop comprising a main stop surface, the main and heel stop surfaces having conforming surfaces when brought into contact with each other,
wherein the main and heel stop surfaces are operable to move towards each other until they come into contact when walking, the distal end of the heel spring element flexing more than an end proximate a mid-portion of the base body; and
a cosmetic,
wherein the prosthetic foot is configured to be disposed at least partially within the cosmetic.

18. The prosthetic foot according to claim 1, where the heel spring element has a shape that tapers from a thick cross section downward towards the distal end thereof.

* * * * *